United States Patent [19]

Nohira et al.

[11] Patent Number: 5,191,112

[45] Date of Patent: Mar. 2, 1993

[54] PROCESS FOR OPTICAL RESOLUTION OF (±)-2-(3-BENZOYL)-PHENYLPROPIONIC ACID

[75] Inventors: Hiroyuki Nohira, Urawa; Kazutaka Arai, Funabashi, both of Japan

[73] Assignee: Nissan Chemical Industries, Ltd., Toyko, Japan

[21] Appl. No.: 571,871

[22] Filed: Aug. 24, 1990

[30] Foreign Application Priority Data

Oct. 17, 1989 [JP] Japan .................................. 1-269466

[51] Int. Cl.$^5$ ............................................. C07B 57/00
[52] U.S. Cl. ................................. 562/401; 562/402; 562/460
[58] Field of Search ........................ 562/401, 402, 460

[56] References Cited

U.S. PATENT DOCUMENTS

| | | | |
|---|---|---|---|
| 4,417,070 | 11/1983 | Arai et al. | 562/56 |
| 4,724,102 | 2/1988 | Cannato et al. | 562/401 |
| 4,752,417 | 6/1988 | Inoue et al. | 562/401 |
| 4,865,770 | 9/1989 | Piselli | 562/402 |
| 4,973,745 | 11/1990 | Blaschke et al. | 562/401 |
| 4,983,765 | 1/1991 | Lukas et al. | 562/401 |

*Primary Examiner*—José G. Dees
*Assistant Examiner*—Vera C. Clarke
*Attorney, Agent, or Firm*—Oliff & Berridge

[57] ABSTRACT

Optical resolution of (±)-2-(3-benzoyl)-phenylpropionic acid is attained effeciently in high yield by the use of a specific optically active amine which is represented by the general formula [I]:

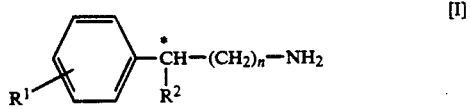

wherein R$^1$ either stands for a hydrogen atom, a chlorine atom, a bromine atom, a methyl group, or an isopropyl group or participates, as a divalent group, in forming a benzene ring in combination with two carbon atoms adjoining each other in a benzene ring to which the substituent, R$^1$, is bonded, R$^2$ stands for a lower alkyl group, a hydroxymethyl group, an α-hydroxybenzyl group, or a

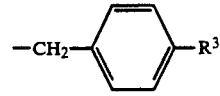

group (R$^3$ standing for a hydrogen atom, a chlorine atom, a bromine atom, or a methyl group), n for 0 or 1, and * for the center of optical activity.

5 Claims, No Drawings

PROCESS FOR OPTICAL RESOLUTION OF (±)-2-(3-BENZOYL)-PHENYLPROPIONIC ACID

BACKGROUND OF THE INVENTION

1. Field of the Invention

This invention relates to a method for the optical resolution of a (±)-2-(3-benzoyl)-phenylpropionic acid [namely a racemate].

The (±)-2-(3-benzoyl)-phenylpropionic acid possesses an anti-inflammatory activity and an analgesic-antipyretic activity and finds utility as a medicine called as "ketoprofen."

2. Description of the Prior Art

As respects the physiological activity of this optically active compound, it has been known that the (+)-2-(3-benzoyl)phenylpropionic acid is more active than the (−)-2-(3-benzoyl)phenylpropionic acid [Farumashia, Vol. 11, No. 7, page 517, 1975] and, unlike other profenes which, in the human body, easily allow isomerization of their inefficaceous R forms [(−) forms] into their efficaceous S forms [(+) forms], the 2-(3-benzoyl)-phenylpropionic acid is difficult to isomere in this kind [R. T. Foster et al., J. Pharm. Sci., 77, 70–73 (1988)]. There has been expressed a desire for a practical method for the production of an optically active 2-(3-benzoyl)-phenylpropionic acid, particularly (+)-2-(3-benzoyl)-phenylpropionic acid.

As a means for producing an optically active 2-(3-benzoyl)phenylpropionic acid, a method which comprises causing (±)-2-(3-benzoyl)-phenylpropionic acid to react with optically active 1-phenylethyl amine thereby synthesizing an amide, separating a diastereomer from the amide by liquid chromatography using silica gel, and oxidatively hydrolyzing the diastereomer with nitrogen dioxide (N$_2$O$_4$) [N. Blazevic et al., Acta Pharm. Jugoslav., 25, 155, (1975)] has been known to the art.

This method, however, does not deserve to be called a commercially feasible approach because it suffers from various disadvantages that the synthesis of the amide necessitates expensive dicyclohexyl carbodimide, that the separation of the diastereomer requires column chromatography and, moreover, the separation itself is attained only with difficulty, that the inevitable oxidative hydrolysis of the diastereomer requires the nitrogen dioxide and entails partial racemization, and that the 1-phenylethyl amine is deprived of optical activity in the course of the hydrolysis and, therefore, cannot be used again.

It, further, has a drawback that reuse of unnecessary diastereomer is not easy to attain.

The high-performance liquid chromatographic method known as a method of analysis directed to optical purity may be utilized for optical resolution. It does not fit mass production because it necessitates an expensive carrier [Ôi et al, Bunseki Kagaku, Vol. 35, page 312, 1986 and B. Sallustio et al., J. Chromatogr., 374, 329. (1986)].

The present inventors have made a diligent study on the problem on the optical resolution of (±)-2-(3-benzoyl)-phenylpropionic acid mentioned above and have consequently perfected the present invention.

SUMMARY OF THE INVENTION

This invention is directed to a method for the optical resolution of (±)-2-(3-benzoyl)-phenylpropionic acid by the use of an optically active amine represented by the general formula [I]:

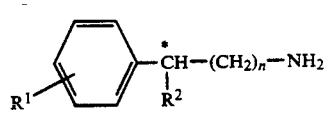

[I]

wherein R$^1$ either stands for a hydrogen atom, a chlorine atom, a bromine atom, a methyl group, or an isopropyl group or participates, as a divalent group, in forming a benzene ring in combination with two carbon atoms adjoining each other in a benzene ring to which the substituent, R$^1$, is bonded, R$^2$ stands for a lower alkyl group, a hydroxymethyl group, an α-hydroxybenzyl group, or a

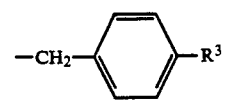

group (R$^3$ standing for a hydrogen atom, a chlorine atom, a bromine atom, or a methyl group), n for 0 or 1, and * for the center of optical activity. More particularly, this invention concerns a method which effects optical resolution of (±)-2-(3-benzoyl)-phenylpropionic acid by causing either of the optically active forms [(+) form or (−) form] to react with optically active amine thereby giving rise to a diastereomer salt and making use of the difference in solubility.

In the optically active amine of the general formula [I] mentioned above, the

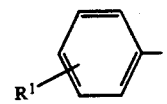

groups wherein R$^1$ participates, as a divalent group, in forming a benzene ring in combination with two carbon atoms adjoining each other in a benzene ring to which the substituent, R$^1$ is bonded include n-naphthyl group, 2-naphthyl group, 1-chloro-2-naphthyl group, and 6-methoxy-2-naphthyl group, for example.

The lower alkyl groups represented by R$^2$ include methyl group, ethyl group, propyl group, isopropyl group, cyclopropyl group, and butyl group, for example.

Though the amount of the optically active amine of the general formula [I] to be used is not specifically defined, the optically active compound [(+) form or (−) form] of high purity can be generally obtained with high efficiency by using the optically active amine in the range of 0.8 to 1.2 equivalent weight, based on 1 equivalent weight of the (±)-2-(3-benzoyl)-phenylpropionic acid.

The present invention is embodied by a procedure which comprises thermally dissolving (±)-2-(3-benzoyl)-phenylpropionic acid and optically active amine of the general formula [I] in a liquid diluent selected from among water, methanol, ethanol, 2-propanol, acetone, 2-butanol, ethyl acetate, dioxane, hexane, chloroform, dichloroethane, anisol, and various mixtures thereof, cooling the resultant hot solution thereby preparing a super-saturated solution, optionally adding thereto as seed crystals the salt (diastereomer salt) of an optically active 2-(3-benzoyl)phenylpropionic acid [(+) form or (−) form] with an optically active amine of the general formula [I], and inducing crystallization of the diastereomer salt.

The diastereomer salt is separated and then, when necessary, subjected to recrystallization. By treating the diastereomer salt with a base such as sodium hydroxide, potassium hydroxide, or ammonium hydroxide, and extracting it from an organic solvent such as diethyl ether, methylene chloride, chloroform, benzene, or toluene, the optically active amine of the general formula [I] is recovered.

From the mother liquor, the optically active 2-(3-benzoyl)phenylpropionic acid [(+) form of (−) form] can be obtained by acidifying the mother liquor with a mineral acid such as hydrochloric acid or sulfuric acid, extracting the acidified mother liquor from an organic solvent such as diethyl ether, methylene chloride, chloroform, benzene, or toluene, drying and concentrating the resultant extract.

Owing to the use of an optically active amine of the general formula [I], a desired optically active 2-(3-benzoyl)phenylpropionic acid [(+) form or (−) form] can be easily obtained in a high yield from (±)-2-(3-benzoyl)phenylpropionic acid.

Now, the present invention will be described more specifically below with reference to working examples. It should be noted, however, that this invention is not limited by these examples.

The optical purity of the produced optically active 2-(3-benzoyl)-phenylpropionic acid [(+) form or (−) form] was determined by the following method developed by the present inventors. Method for determination of optical purity In hexane, (±)-2-(3-benzoyl)-phenylpropionic acid, 1-butanol, and a catalytic amount of concentrated sulfuric acid were stirred to prepare a butyl ester. By subjecting this butyl ester to separation an optical with an optical resolution column [produced by Daicel Chem. Ind., Ltd. and marketed under trademark designation of "Chiralcel OB") using a hexane: 2-propanol (9:1) at a flow rate of 1.0 ml/min, the optical purity could be determined because the retention time of the butyl ester of the R form was 8.9 minutes and that of the butyl ester of the S form was 12.8 minutes.

EXAMPLE 1

Optical resolution by the use of (−)-1-phenylpropyl amine in 44.5 ml of ethyl acetate, 12.7 g of (±)-2-(3-benzoyl)-phenylpropionic acid and 6.7 g of (−)-1-phenylpropyl amine were dissolved and left crystallizing at 20° C. By separating the crystals by filtration, there was obtained 12.1 g of colorless crystalline diastereomer salt $\{[\alpha]_D^{25}+4.3°\ (c=1.04,\ \text{methanol})\}$.

The diastereomer salt thus obtained was dissolved in 109.2 ml of ethyl acetate, left crystallizing at 20° C., and filtered to obtain 5.59 g of a colorless crystalline diastereomer salt $\{[\alpha]_D^{25}+1.3°\ (c=1.12,\ \text{methanol})\}$.

The diastereomer salt thus obtained was further dissolved in 92.7 ml of ethyl acetate, left crystallizing at 20° C., and then filtered, to obtain 4.36 g (22% in yield) of colorless crystalline diastereomer salt having a melting pont of 132° to 134° C. $\{[\alpha]_D^{25}\pm0.0°\ (c=1.23,\ \text{methanol})\}$.

By adding 16.5 ml of an aqueous 1N sodium hydroxide solution to the diastereomer salt, there was induced liberation of (−)-1-phenylpropyl amine. This amine was removed by extraction twice with 10 ml of toluene. The residue of this extraction was acidified with 8.3 ml of 3N hydrochloric acid and then extracted three times with 10 ml of diethyl ether.

The extract was dried with anhydrous magnesium sulfate and then concentrated, to obtain 2.79 g of colorless crystalline (+)-2-(3-benzoyl)-phenylpropionic acid [44% in yield relative to the (+) compound in the starting material].

The product had an optical purity of not less than 99% ee and a melting point of 69° to 71° C. $\{[\alpha]_D^{25}+53.6°\ (c=1.02,\ CH_2Cl_2)\}$.

NMR (60 MHz, CDCl$_3$) δ1.52 (d, J=7 Hz, 3H), 3.77 (q, J=7 Hz, 1H), 7.3 to 7.8 (m, 9H), 11.6 (broad, 1H)

EXAMPLE 2

Optical resolution by the use of (+)-1-phenylethyl amine

In 9 ml of ethanol, 2.54 g of (±)-2-(3-benzoyl)phenylpropionic acid was dissolved. The resultant solution and 1.21 g of (+)-1-phenylethyl amine added thereto were thermally dissolved. The resultant hot solution was cooled to 16° C. and stirred and, at the same time, left crystallizing. The crystals consequently formed were separated by filtration and washed twice with 2 ml of ethanol, to obtain 1.39 g of colorless crystalline diastereomer salt (37.5 in yield).

By adding 5 ml of an aqueous 1N sodium hydroxide solution to this diastereomer salt, there was induced liberation of (+)-1-phenylethyl amine. This amine was removed by extraction twice with 10 ml of toluene. The residue of this extraction was acidified with 3 ml of 3N hydrochloric acid and extracted three times with 10 ml of diethyl ether.

The resultant extract was dried with anhydrous magnesium sulfate and concentrated, to obtain 0.46 g of colorless crystalline (−)-2-(3-benzoyl)-phenylpropionic acid [36% in yield relative to the (−) compound in the starting material].

The product had an optical purity of not less than 12% ee and a melting point of 90° to 94° C. $\{[\alpha]_D^{25}-6.5°\ (c=1.02,\ CH_2Cl_2)\}$. The other analytical values were the same as those obtained in Example 1.

EXAMPLES 3 TO 6

Optical resolution of (±)-2-(3-benzoyl)-phenylpropionic acid was carried out by following the procedure of Example 1, except a variety of optically active amines were used instead. The yields of diastereomer salts produced are shown in Table 1 and the yields and various properties of the produced optically active compounds are shown in Table 2.

The optically active amines used as a resolving agent were 1-phenylethyl amine (PEA), 1-phenyl-2-(4-methylphenyl)-ethyl amine (PTE), 1-(1-naphthyl)-ethyl amine (NEA), and 2-(4-methylphenyl)-3-methylbutyl amine (MTBA) severally represented by the following structural formulas.

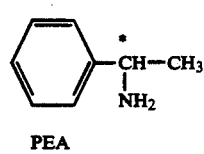

PEA

-continued

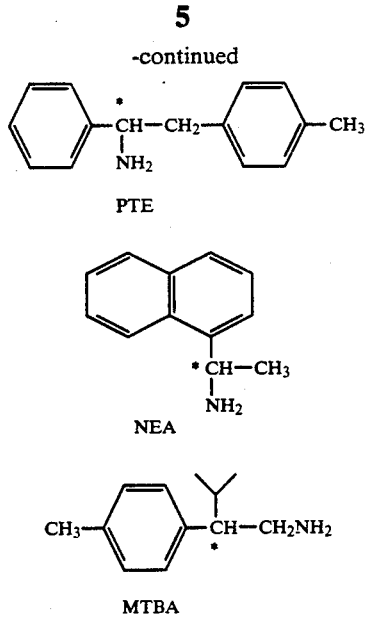

Table 1 shows the data concerning the diastereomer salts formed of the produced optically active amines with an optically active 2-(3-benzoyl)-phenylpropionic acid [(+) form or (−) form] and Table 2 those concerning (+)-2-(3-benzoyl)-phenylpropionic acid or (−)-2-(3-benzoyl)-phenylpropionic acid obtained from the diastereomer salts of Table 1. The example numbers given in 1 correspond to those given in Table 2.

EXAMPLES 7 TO 12

Optical resolution of (±)-2-(3-benzoyl)-phenylpropionic acid was carried out by following the procedure of Example 1, except a variety of optically active amines were used instead. The yields of diastereomer salts produced are shown in optical purity and sign of form of each of the produced optically active compounds are shown in Table 3.

The optically active amines used as a resolving agent were 1-(4-methylphenyl)-ethyl amine (MPEA), erythro-1,2-diphenyl-2-hydroxyethyl amine (DPHE), and 1-phenylpropyl amine (PPA) severally represented by the following structural formulas.

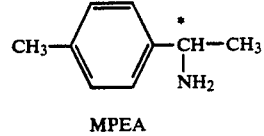

MPEA

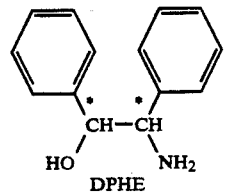

DPHE

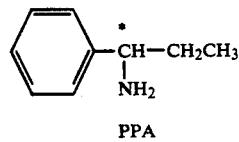

PPA

TABLE 1

| | | | | Produced diasteromer salt | | |
|---|---|---|---|---|---|---|
| Example | Resolving agent | Solvent (ml/g of diastereomer salt) | | Yield[3] (%) | Melting point (°C.) | $[\alpha]_D^{25}$ (c = 1.00, MeOH) |
| 3 | (−)-PEA | Ethyl acetate[1] | 4.8 | 137 | 101∼104 | −3.4 |
| | | Ethyl acetate[2] | 3.9 | 57 | 104∼106 | −3.0 |
| 4 | (−)-PTE | 2-Propanol (IPA)[1] | 19.9 | 112 | 129∼133 | −47 |
| | | 2-Propanol[2] | 11.1 | 77 | 133∼135 | −49 |
| 5 | (−)-NEA | Ethyl acetate: IPA (2.3:1)[1] | 10.7 | 91 | 129∼135 | −2.7 |
| | | Ethyl acetate: IPA (5:4)[2] | 18.9 | 26 | 142∼144 | ±0.0 |
| 6 | (+)-MTBA | 2-Propanol[1] | 5.8 | 184 | 125∼127 | +8.0 |
| | | Methanol[2] | 3.1 | 66 | 131∼134 | +13.1 |

Note:
[1] Amount of solvent, based on calculated amount of total diastereomer salt
[2] Amount of solvent used for recrystallization of produced diastereomer salt
[3] The yield was calculated with the amount of the (+) form or (−) form equal to one half of the amount of (±)-2-(3-benzoyl)-phenylpropionic acid taken as 100%.

TABLE 2

| 2-(3-benzoyl)-phenylpropionic acid [(+) form or (−) form] | | | | |
|---|---|---|---|---|
| Example | Yield (%)[1] | Melting point (°) | $[\alpha]_D^{25}$ (°) (c = 1.00, CH$_2$Cl$_2$) | Optical purity (% ee)[2] |
| 3 | 31 | 90∼94 | +6.1[3] | 11 |
| 4 | 64 | 89∼92 | +9.1[3] | 17 |
| 5 | 22 | 75∼82 | −28.4[4] | 53 |
| 6 | 45 | — | −37.0[4] | 69 |

Note:
[1] The yield was calculated with the amount of the (+) form or (−) form equal to one half of the amount of (±)-2-(3-benzoyl)-phenylpropionic acid taken as 100%.
[2] The optical purity was calculated with $(\alpha)_D^{25}$ ± 54.0° (c = 1.00, CH$_2$Cl$_2$) taken as 100%.
[3] + for (+)-2-(3-benzoyl)-phenylpropionic acid
[4] − for (−)-2-(3-benzoyl)-phenylpropionic acid

TABLE 3

| | | | Yield of produced diastereomer (%)[4] | Optically active 2-(3-benzoyl)-phenylpropionic acid | |
|---|---|---|---|---|---|
| Example | Resolving agent | Solvent (ml/g of diastereomer salt) | | Optical purity (% ee)[5] | sign of form[6] |
| 7 | (+)-MPEA | 2-Propanol:isopropyl ether (1:1) | 81 | 8.0 | + |
| 8 | (−)-DPHE | Ethyl acetate:ethanol | 100 | 38 | − |

TABLE 3-continued

| Example | Resolving agent | Solvent (ml/g of diastereomer salt) | Yield of produced diastereomer (%)[4] | Optically active 2-(3-benzoyl)-phenylpropionic acid Optical purity (% ee)[5] | sign of form[6] |
|---|---|---|---|---|---|
| | | (1:1) | | | |
| 9 | (−)-PPA | Anisole 1.29[1] | 112 | 19.6 | + |
| 10 | (−)-PPA | Dioxane 1.6[1] 1.2[2] | 26 | 73 | + |
| 11 | (−)-PPA | Dichloroethane 3.2[1] 2.4[2] 2.1[3] | 7.2 | 93.7 | + |
| 12 | (−)-PPA | 2-Butanone 1.3[1] | 81 | 36.9 | + |

Note:
[1] Amount of solvent, based on calculated amount of total diastereomer salt
[2] Amount of solvent used for recrystallization of produced diastereomer salt
[3] Amount of solvent used for second recrystallization of formed diastereomer salt
[4] The yield was calculated with the amount of the (+) form or (−) form equal to one half of the amount of (±)-2-(3-benzoyl)-phenylpropionic acid taken as 100%.
[5] This property was verified based on the integral ratio of the signal of Si—$CH_3$ in the H-NMR of the amide [A] of with (benzylmethylphenylsilyl)-methyl amine. On this basis, the standard specific rotation, $[\alpha]_D^{25}$ (+) and (−), of (+) and (−)-2-(3-benzoyl)-phenylpropionic acids was found to be 53.6° (c = 1.00, $CH_2Cl_2$).

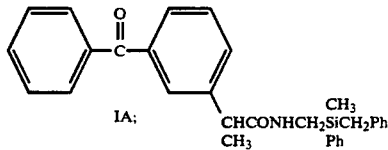

IA; $CHCONHCH_2SiCH_2Ph$ with $CH_3$ and Ph substituents

[6] + for (+)-2-(3-benzoyl)-phenylpropionic acid and − for (−)-2-(3-benzoyl)-Phenylpropionic acid.

What is claimed is:

1. A method for the optical resolution of (±)-2-(3-benzoyl)-phenylpropionic acid comprising dissolving (±)-2-(3-benzoyl)-phenylpropionic acid into a solvent; adding an optically active phenylpropylamine; inducing crystallization; and filtering the resulting crystals to obtain a diastereomer salt, treating said diastereomer salt with a base, and subsequently acidifying said diastereomer salt to obtain a residue, and drying said residue to obtain a (−)-2-(3-benzoyl)-phenylpropionic acid.

2. The method of claim 1 wherein a mixture of said (±)-2-(3-benzoyl)-phenylpropionic acid dissolved in said solvent and said added optically active phenylpropylamine is heated prior to crystallization, and then allowed to cool.

3. The method of claim 2, wherein a diastereomer salt of an optically active 2-(3-benzoyl)-phenylpropionic acid with an optically active phenylpropylamine is added to the solvent in the form of seed crystals.

4. The method of claim 1, wherein said solvent is selected from the group consisting of hexane, chloroform, dichloroethane, and mixtures thereof.

5. The method of claim 1, wherein said residue is extracted from an organic solvent selected from the group consisting of diethyl ether, methylene chloride, chloroform, benzene and toluene.

* * * * *